(12) United States Patent
Yoon et al.

(10) Patent No.: US 8,961,935 B2
(45) Date of Patent: Feb. 24, 2015

(54) MRI CONTRAST AGENT COATED WITH CARBOXYLATED MANNAN AND METHOD FOR PRODUCING THE SAME

(75) Inventors: Seong Jun Yoon, Seoul (KR); Soo Youn Jun, Seoul (KP); An Sung Kwon, Gwangju (KR); Sang Hyeon Kang, Seoul (KR); Yong Yeon Jeong, Gwangju (KR); In Kyu Park, Gwangju (KR); Chong Su Cho, Seoul (KR); You Kyoung Kim, Seoul (KR); Won Jong Kim, Gyeongsangbuk-Do (KR); Ran Namgung, Gyeongsangbuk-Do (KR)

(73) Assignee: Intron Biotechnology, Inc. (KR)

( * ) Notice: Subject to any disclaimer, the term of this patent is extended or adjusted under 35 U.S.C. 154(b) by 137 days.

(21) Appl. No.: 13/087,816

(22) Filed: Apr. 15, 2011

(65) Prior Publication Data
US 2012/0230919 A1    Sep. 13, 2012

(30) Foreign Application Priority Data

Mar. 8, 2011   (KR) .................. 10-2011-0020164

(51) Int. Cl.
| | |
|---|---|
| A61K 49/06 | (2006.01) |
| B82Y 40/00 | (2011.01) |
| B82Y 5/00 | (2011.01) |
| A61K 49/18 | (2006.01) |
| B82Y 15/00 | (2011.01) |

(52) U.S. Cl.
CPC ............. *A61K 49/1863* (2013.01); *B82Y 15/00* (2013.01); *B82Y 40/00* (2013.01); *Y10S 977/773* (2013.01); *Y10S 977/93* (2013.01); *Y10S 977/89* (2013.01)
USPC ....... 424/9.35; 424/9.323; 977/773; 977/930; 977/890

(58) Field of Classification Search
CPC ........... A61K 49/1863; A61K 49/1821; A61K 49/1851
See application file for complete search history.

(56) References Cited

U.S. PATENT DOCUMENTS

| | | | |
|---|---|---|---|
| 5,262,176 A | 11/1993 | Palmacci et al. | |
| 5,462,053 A | 10/1995 | Briggs et al. | |
| 5,492,814 A * | 2/1996 | Weissleder ................... | 435/7.25 |
| 5,766,572 A * | 6/1998 | Hasegawa et al. ......... | 424/9.322 |
| 7,569,556 B2 * | 8/2009 | Narayan et al. ................. | 514/57 |
| 2003/0092608 A1 * | 5/2003 | Kawaguchi et al. ............. | 514/8 |

FOREIGN PATENT DOCUMENTS

| | | |
|---|---|---|
| EP | 0526503 B1 * | 4/1991 |
| EP | 0284549 B1 * | 7/1992 |
| KR | 10-0949465 A | 8/2009 |

OTHER PUBLICATIONS

Bautista et al., Surface characterisation of dextran-coated iron oxide nanoparticles prepared by laser pyrolysis and coprecipitation, J. Magn. Mater. 293:20-27 (2005).
Chang et al., Preparation and adsorption properties of monodisperse chitosan-bound Fe3O4 magnetic nanoparticles for removal ofCu(II) ions, J. Colloid Interface Sci. 283:446-451 (2005).
Chastellain et al., Particle size investigations of a multistep synthesis of PVA coated superparamagnetic nanoparticles, J. Colloid Interface Sci. 278(2):353-360 (2004).
Lee et al., Artificially engineered magnetic nanoparticles for ultra-sensitive molecular imaging, Nat. Med. 13(1):95-99 (2007).
Liao et al., Preparation and characterization of a novel magnetic nano-adsorbent, J. Mater. Chem., 12:3654-3659 (2002).
Nasongkia et al., Multifunctional Polymeric Micelles as Cancer-Targeted, MRI-Ultrasensitive Drug Delivery Systems, Nano Lett. 6(11): 2427-2430 (2006).
Wang et al., Superparamagnetic iron oxide contrast agents: physicochemical characteristics and applications in MR imaging, Eur. Radiol. 11:2319-2331 (2001).
Research in Progress Seminar Series, Clinical Vaccine R&D Center, Chonnam National University dated Apr. 12, 2010.

* cited by examiner

*Primary Examiner* — Michael G Hartley
*Assistant Examiner* — Lance Rider
(74) *Attorney, Agent, or Firm* — Meunier Carlin & Curfman, LLC (57) ABSTRACT

The present invention relates to a magnetic resonance imaging (MRI) contrast agent coated with carboxylated mannan, particularly a carboxylated mannan coated superparamagnetic MRI contrast agent specifically targeting antigen presenting cells and having excellent in vivo stability, and a method for producing the same. The MRI contrast agent coated with carboxylated mannan of the present invention can provide excellent in vivo stability and biocompatibility owing to its high surface negative charge, and can be introduced specifically into antigen presenting cells owing to mannose of mannan, so as to visualize the antigen presenting cells and the tissue containing the antigen presenting cells in MRI.

18 Claims, 8 Drawing Sheets
(6 of 8 Drawing Sheet(s) Filed in Color)

Cm-mannan 10 SPION

Dextran SPION

PVA SPION

FIG. 11

MRI CONTRAST AGENT COATED WITH CARBOXYLATED MANNAN AND METHOD FOR PRODUCING THE SAME

CROSS REFERENCE TO RELATED APPLICATIONS

This application claims the benefit of of priority to Korean patent application No. 10-2011-0020164, filed Mar. 8, 2011, which application is incorporated by reference herein in its entirety.

FIELD

The present invention relates to a magnetic resonance imaging (MRI) contrast agent, particularly a MRI contrast agent that can be introduced specifically into antigen presenting cells for visualization of the antigen presenting cells and the tissue containing the antigen presenting cells in MRI. More precisely, the present invention relates to a superparamagnetic MRI contrast agent coated with carboxylated mannan.

BACKGROUND

MRI, the most representative tomography technique, is the method to obtain 3-dimensional images non-invasively that has been widely used for the diagnosis of disease owing to its excellent contrast and spatial resolution.

MRI contrast agents are a group of contrast media used to improve the visibility of internal body structures by increasing contrast between normal tissues and abnormal tissues in MRI. MRI contrast agents alter the T1 and T2 relaxation times of tissues and body cavities where they are present. Depending on the image weighting, this can give a higher or lower signal. Most MRI contrast agents work through shortening the relaxation time of protons located nearby. Generally, MRI contrast agents are divided into two groups: paramagnetic contrast agents and superparamagnetic contrast agents (Eur. Radiol. 11: 2319, 2001).

The toxicity of paramagnetic contrast agent is an important concern. It can only produce images at mM level. So, the superparamagnetic contrast agent that can produce high-sensitive images at $\mu$M level draws our attention (Nano Lett. 6: 2427, 2006; Nat. Med. 13: 95, 2007).

The superparamagnetic contrast agent widely used in clinical is prepared by using superparamagnetic nanoparticles represented by such superparamagnetic iron oxide (SPIO) as magnetite ($Fe_3O_4$) and maghemite ($Fe_2O_3$). This agent is prepared as the form of ferrofluid that is stable colloid comprising even particles less than scores of nanometer in size so as to be injected in the body.

The pure superparamagnetic iron oxide particle (1) is hydrophobic and shows the high ratio of volume to surface area, suggesting the strong hydrophobic interaction and coagulation that can form a cluster easily; (2) has low stability, so that the original structure can easily be changed, suggesting that its magnetic characteristics can be easily changed; (3) is easily bio-degraded when it is exposed on so called bio-environment; and (4) does harm on human body because pure iron oxide itself is toxic. Therefore, surface modification of the particle is required to overcome the said problems and to improve stability of ferrofluid containing the superparamagnetic nanoparticles.

For the surface modification, it has been tried to coat the surface with various polymers. As a result, the MRI contrast agents coated with dextran or dextran derivatives have been commercialized. The conventional coating materials are exemplified by such synthetic polymers (J. Mater. Chem. 12: 3654-3659, 2002; J. Colloid Interface Sci. 278: 353-360, 2004) as Polyacrylic acid (PAA), Polyvinylpyrrolidone (PVP), Polyvinylalcohol (PVA), and Polyethylene glycol (PEG); and such natural polymers (J. Colloid Interface Sci. 283: 446-451, 2005; J. Magn. Mater. 293: 20-27, 2005) as Gelatin, Chitosan, and Pullulan, in addition to dextrans.

Mannan is not a material that is widely used. However, it was reported that mannan was used for surface modification (coating) (U.S. Pat. No. 5,262,176; and U.S. Pat. No. 5,462,053). The present inventors had also used mannan previously (Korean Patent No. 10-0949465). U.S. Pat. No. 5,262,176 describes the purpose of use of mannan. In this description, like other conventional polymer coating, the improvement of in vivo stability of iron oxide colloid is the issue. U.S. Pat. No. 5,462,053 also describes the concern about stability of a contrast agent suspension, as the case of other conventional polymer coating. Korean Patent No. 10-0949465 describes the purpose of targeting by a mannose specific receptor, in addition to the generally expected effect of the conventional polymer coating. However, there are problems in the use of mannan, which are biotoxicity and trap in circulation system in vivo. Therefore, it is important to develop a novel mannan derivative that has biocompatibility and low biotoxicity but long half-life in vivo and also to develop a novel MRI contrast agent coated with such mannan derivative.

If specific contrast-enhancement of antigen presenting cells or target tissue that contains a large number of antigen presenting cells by MRI is possible, the clinical usage of it can be definitely increased. In general, cancer tissues or lesion of septic shock has increased number of antigen presenting cells. So, if a large number of antigen presenting cells are detected in a specific area, it suggests that something abnormal is going on. Therefore, it is clinically very important to develop a diagnostic technique to detect any abnormality using the antigen presenting cells.

Numbers of papers and patent descriptions have been cited in this description and the citation is marked in parentheses. The descriptions of cited papers and patent documents are attached in this invention so that the art and text of this invention can be more clearly understood.

SUMMARY

The present invention relates to a magnetic resonance imaging (MRI) contrast agent coated with carboxylated mannan, particularly a carboxylated mannan coated superparamagnetic MRI contrast agent specifically targeting antigen presenting cells and having excellent in vivo stability, and a method for producing the same. The MRI contrast agent coated with carboxylated mannan of the present invention can provide excellent in vivo stability and biocompatibility owing to its high surface negative charge, and can be introduced specifically into antigen presenting cells owing to mannose of mannan, so as to visualize the antigen presenting cells and the tissue containing the antigen presenting cells in MRI.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein.

DESCRIPTION

It is an object of the present invention to overcome the problems of the prior art and thus to develop a technique and method long requested.

Precisely, it is an object of the present invention to provide a MRI contrast agent that has excellent in vivo stability, safety, and tissue specific contrast-enhancement ability of antigen presenting cells or the tissue containing antigen presenting cells, and a method for producing the same.

It is another object of the present invention to provide a MRI contrast agent that can be used for the diagnosis of cancer metastasis to lymph node.

It is a further object of the present invention to provide a MRI contrast agent that can be used for the diagnosis of sepsis.

To overcome the disadvantages of the MRI contrast agent coated with the common mannan, the present inventors introduced carboxyl group into mannan. The present inventors expected that the MRI contrast agent coated with such carboxylated mannan could lower toxicity and increase in vivo half-life. Thus, the inventors develop a method to introduce carboxyl group enough into mannan and then completed this invention by confirming that the MRI contrast agent coated with carboxylated mannan was safer in use than the MRI contrast agents coated with the common mannan.

So, the present invention provides a superparamagnetic nanoparticle MRI contrast agent coated with carboxylated mannan having excellent in vivo stability, safety and increased specific contrast-enhancement ability for antigen presenting cells or the tissue containing antigen presenting cells, and a method for producing the same.

As a magnetic material for the superparamagnetic nanoparticle, manganese oxide (MnO), manganese ferrite ($MnFe_2O_4$), iron-platinum (Fe—Pt) alloy, cobalt-platinum (Co—Pt) alloy or cobalt (Co) can be selected, but superparamagnetic iron oxide (SPIO) such as magnetite ($Fe_3O_4$) or maghemite ($Fe_2O_3$) is more preferred.

The said antigen presenting cells can be selected among dendritic cells, macrophages, and B-cells, but the cells having mannose receptor are preferred, particularly macrophages are more preferred.

The representative example of the usage of the MRI contrast agent of the present invention is cancer diagnosis. Particularly it is more useful for the diagnosis of cancer metastasis to lymph node. The MRI contrast agent of the present invention can also be used for the diagnosis of inflammation-related disease, for example for the diagnosis of sepsis.

The present invention also provides a method for producing the MRI contrast agent having increased contrast-enhancement ability for antigen presenting cells or tissues containing the antigen presenting cells that is coated with carboxylated mannan, which comprises the following steps:

A) synthesizing superparamagnetic nanoparticles;
B) synthesizing aldehyde-mannan by introducing aldehyde group into mannan;
C) preparing carboxylated mannan by oxidizing the aldehyde-mannan; and
D) coating the synthesized superparamagnetic nanoparticles with the prepared carboxylated mannan.

The said aldehyde-mannan indicates the mannan introduced with aldehyde group and the said carboxylated mannan indicates the mannan introduced with carboxyl group.

The present inventors tried a variety of methods to introduce carboxyl group in mannan. As a result, it was confirmed that no other methods than the method of the present invention were successful in introducing carboxyl group enough to the wanted level. Only the method of the present invention that uses aldehyde-mannan described herein was capable of introducing enough carboxyl group (10 mol % of the total mannose were carboxylated). Therefore, the present invention is characterized by providing the MRI contrast agent coated with carboxylated mannan and by using aldehyde-mannan as an intermediate material for the preparation of carboxylated mannan.

The superparamagnetic MRI contrast agent coated with the mannan introduced with carboxyl group at a high level has excellent in vivo stability but low in vivo toxicity, in addition to be able to be introduced specifically into antigen presenting cells, so that it can visualize the antigen presenting cells and the tissue containing the antigen presenting cells specifically in MRI. The MRI contrast agent that is able to visualize antigen presenting cells and the tissue containing the antigen presenting cells specifically and has excellent in vivo stability can be effectively used for the detection of early metastasis of breast cancer, colon cancer and stomach cancer to lymph node and can also be effectively used for the early diagnosis of sepsis.

The accurate diagnosis of cancer metastasis to lymph node is very important for the treatment of cancer and for the judgment of prognosis of a cancer patient. The early diagnosis of sepsis is also very important. To detect cancer metastasis to lymph node, PET-CT (Positron Emission Tomography and Computed Tomography) is widely used at this time. However, MRI provides lower risk of radiation poisoning compared with PET-CT, and can provide early diagnosis of micro-metastasis with excellent spatial resolution.

Sepsis is now diagnosed by ELISA (Enzyme-linked immunosorbent assay), which takes longer time to diagnose, yet. Death rate of sepsis is very high, so the early diagnosis is crucial. The present invention can provide fast and easy diagnosis of sepsis.

As explained hereinbefore, the present invention is to provide a superparamagnetic MRI contrast agent coated with carboxylated mannan which has excellent in vivo stability and dramatically decreased toxicity.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Carboxylated Mannan

Figure 1:
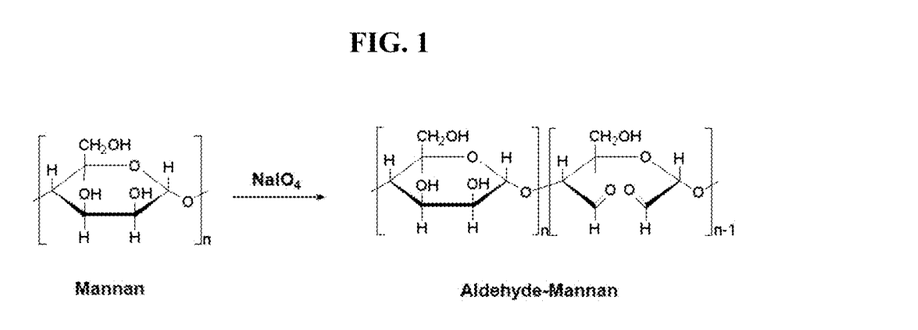
FIG. 1 is a diagram illustrating the synthesis scheme of the aldehyde-mannan of the present invention.

<1-1> Synthesis of Aldehyde-Mannan 400 mg of mannan was dissolved in 16 ml of distilled water. 9 ml of 0.1 M $NaIO_4$ solution (0.4 equivalent to mannose) was added slowly to the mannan solution, followed by reaction for one hour at 4° C. with light blocked. Glycerol (0.8 equivalent to mannose) was added and stirred for 30 minutes to terminate the reaction. The reaction mixture was transferred to dialyzer membrane (MWCO 1,000), followed by dialysis in distilled water at 4° C. for one day. Then, the dialysis solution was freeze-dried to give 393 mg of white solid aldehyde-mannan. The process is illustrated in FIG. 1.

Figure 2:
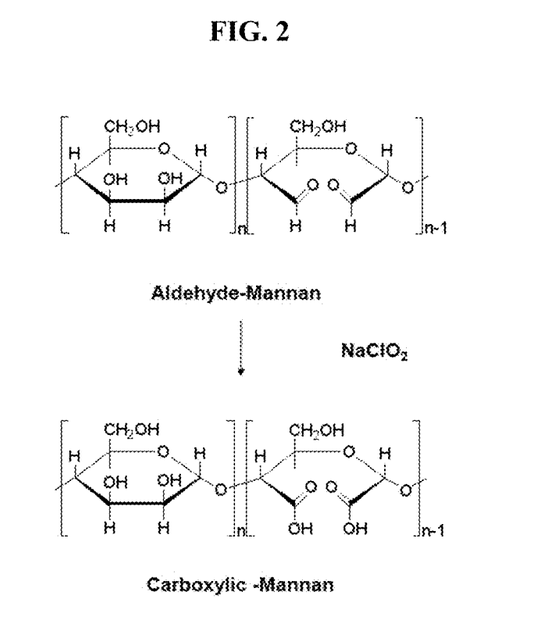
FIG. 2 is a diagram illustrating the synthesis scheme of the carboxylated mannan of the present invention.
Figure 3:
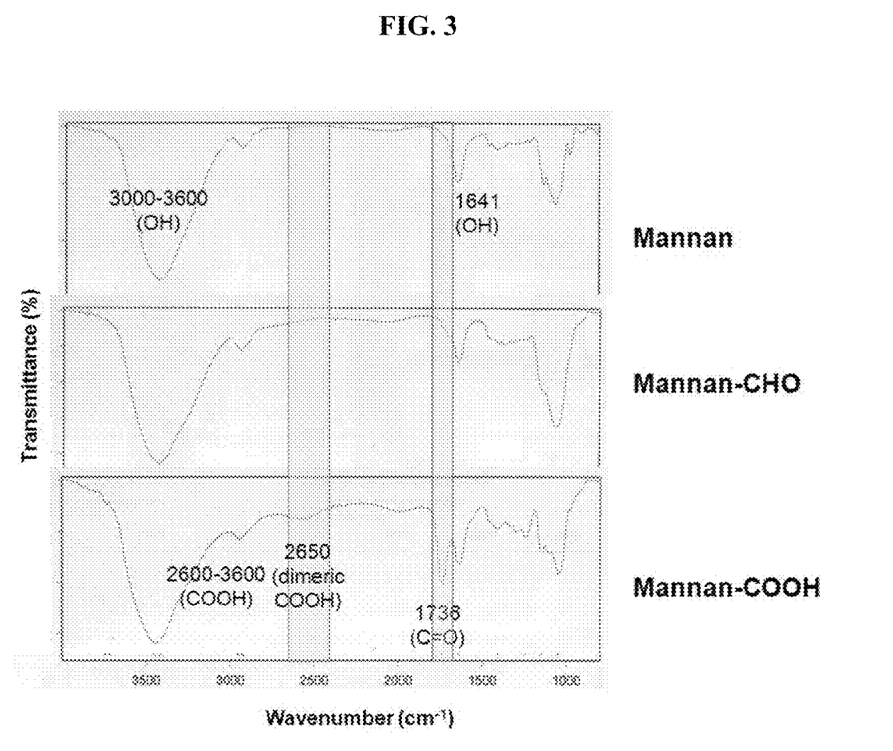
FIG. 3 is a diagram illustrating the result of Fourier Transform Infrared Spectrometry with the aldehyde-mannan and the carboxylated mannan prepared according to the method of the present invention. In this diagram, "Mannan-CHO" indicates aldehyde-mannan, and "Mannan-COOH" indicates carboxylated mannan.

<1-2> Synthesis of Carboxylated Mannan 370 mg of aldehyde-mannan was dissolved in 20 ml of distilled water. This aldehyde-mannan solution was placed in ice water bath, to which $H_2O_2$ (1.2 equivalent to mannose) was added. 3 ml of 0.5 M $NaClO_2$ (1.2 equivalent to mannose) was added slowly to the solution and pH was adjusted to 5. After removing ice water bath, pH of the reaction mixture was maintained as 5 by using NaOH with stirring. When pH was stable without any changes, pH of the reaction mixture was set at 9, followed by dialysis using dialyzer membrane (MWCO 1,000) in distilled water at 4° C. for one day. Then, the dialysis solution was freeze-dried to give 351 mg of white solid carboxylated mannan. Carboxyl group introduced in the produced carboxylated mannan was quantified by using 1M HCl. As a result, it was confirmed that approximately 13 mol % of mannose was carboxylated. The process is illustrated in FIG. 2. Introduction of carboxyl group was confirmed by the conventional analysis with Fourier transform infrared spectrometer (Nicolet Magna 550 series II spectrometer, Midac, Atlanta, Ga., USA) and the result is shown in FIG. 3. FIG. 3 presents the characteristic peak presenting the introduction of carboxyl group.

Example 2

Preparation of Superparamagnetic Iron Oxide Nanoparticles

To produce superparamagnetic iron oxide nanoparticles (SPIONs), $Fe^{2+}$ and $Fe^{3+}$ were reduced with $NH_4OH$ solution, resulting in the precipitation of SPIONs. Particularly, 2 mol $FeCl_3.6H_2O$ and 1 mol $FeCl_2.4H_2O$ were added to 70 ml of distilled water. The mixed solution was vigorously stirred, to which 7 ml of ammonia solution was added. At that time, a black precipitate was formed. This precipitate was fixed with permanent magnet, during which the solution was washed with distilled water until pH was decreased from 10 to 7. Then, pH7 precipitate was obtained.

Figure 4:
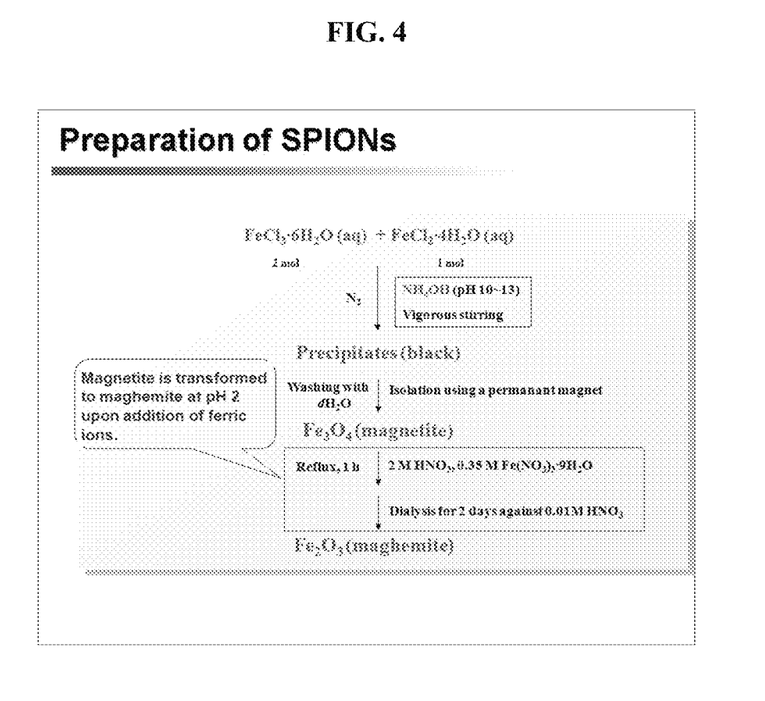
FIG. 4 is a flow chart illustrating the method for producing iron oxide nanoparticles (SPIONs) of the present invention.

20 ml of 2 M $HNO_3$ solution and 30 ml of 0.35 M $Fe(NO_3)_3.9H_2O$ solution were added to the precipitate, followed by oxidation by refluxing for 1 hour. The brown suspension formed by oxidation was dialyzed in 0.01 M nitric acid for 2 days to prepare SPIONs stock solution, which was stored at 4° C. (see FIG. 4).

Example 3

Preparation of Superparamagnetic Iron Oxide Nanoparticles Coated with Carboxylated Mannan The prepared SPIONs stock solution was diluted with distilled water to the concentration of 6.25 mg/ml. The prepared diluted solution was stirred at 4° C. In the meantime, 17.5 mg of carboxylated mannan was dissolved in 200 µl of distilled water to prepare carboxylated mannan solution. 800 µl of the diluted SPIONs stock solution was taken and added to the prepared carboxylated mannan solution slowly drop by drop with stirring the solution at 4° C. Upon completion of the addition, the mixture was stirred at 4° C. for overnight. Finally, a small amount of $NH_4OH$ was added to adjust pH to 7. Then, NaCl was added at the concentration of 0.9% to adjust ionic strength. The prepared solution was used as the carboxylated mannan coated superparamagnetic iron oxide nanoparticle (MRI contrast agent) solution.

As controls, SPIONs coated with mannan, SPIONs coated with dextran, and SPIONs coated with PVA (polyvinyl alcohol) were prepared. All the processes to produce those controls were the same as described in the production of SPIONs coated with carboxylated mannan.

Example 4

Characteristics of Carboxylated Mannan Coated SPIONs

<4-1> Size Distribution of Carboxylated Mannan Coated SPIONs

Figure 5:
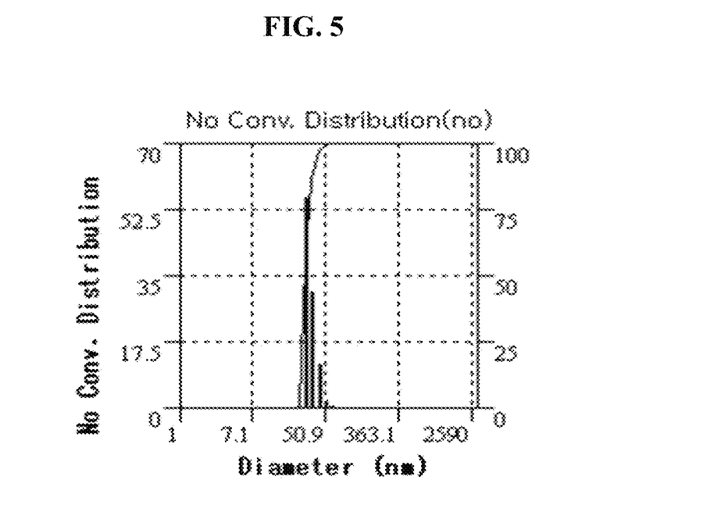
FIG. 5 is a graph showing the result of total light scattering with the SPIONs coated with the carboxylated mannan prepared according to the method of the present invention.

To investigate the size and the distribution of carboxylated mannan coated SPIONs prepared according to the method of the present invention, size distribution was measured by using electrophoretic light scattering spectrophotometer (ELS 8000, Otsuka Electronics, Osaka, Japan; scattering angle: 90°) at 25° C. The sample for the analysis with the electrophoretic light scattering spectrophotometer was prepared as follows: carboxylated mannan coated SPIONs were added to distilled water and then sonicated. As shown in FIG. 5, even particles were regularly distributed and the mean diameter of the particles was 34.1 nm.

<4-2> Measurement of Zeta Potential

Zeta potential (the index indicating surface quantity of electric charge of colloid particles suspended in liquid solution, which is the potential difference between shear boundary and bulk solution) of carboxylated mannan coated SPIONs was measured by the conventional method. As a result, the zeta potential was determined to be −31.69 mV. This zeta potential indicated that the solution of carboxylated mannan coated SPIONs was in stable condition, compared with the conventional colloid solution.

Example 5

Comparison with Controls

<5-1> Toxicological Comparison with Mannan Coated SPIONs

Toxicological comparison was performed with carboxylated mannan coated SPIONs and mannan coated SPIONs by using conventional single-dose intravenous toxicity test. The test was performed at Korea Institute of Toxicology, Korea Research Institute of Chemical Technology. Particularly, carboxylated mannan coated SPIONs or mannan coated SPIONs were administered to 7 weeks old ICR mice (5 male mice and 5 female mice per group) at different doses of 20, 40, and 80 mg Fe/kg by intravenous injection. General symptoms, death, and weight changes in mice were observed for 15 days. Then, any abnormal signs in internal organs were checked by autopsy.

Some of those mice administered with mannan coated SPIONs at the dose of at least 20 mg Fe/kg were dead or demonstrated subdued behavior, irregular respiration, prone position and lower abdomen contamination. Based on these results, fifty percent lethal dose ($LD_{50}$) of mannan coated SPIONs was determined to be 44 mg Fe/kg in both male and female mice. In the meantime, none of those experimental group mice including both male and female administered with carboxylated mannan coated SPIONs were dead and any specific abnormality was not observed either. Therefore, it was suggested that $LD_{50}$ of carboxylated mannan coated SPIONs was more than 80 mg Fe/kg in mice.

The above result indicates that carboxylated mannan coated SPIONs are much safer MRI contrast agent than mannan coated SPIONs.

<5-2> Measurement of Uptake into Antigen Presenting Cells

To take antigen presenting cells or the tissue containing a large amount of such antigen presenting cells as the target of MRI, an MRI contrast agent needs to be successfully introduced into antigen presenting cells. If the contrast agent is specific to the target, it would be more preferred. Following experiments were performed to confirm the successful intracellular uptake.

Figure 6:
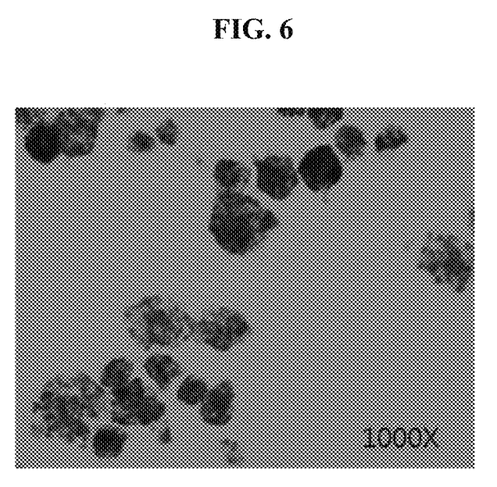
FIG. 6 is a Prussian blue staining result of examining intracellular uptake of the SPIONs coated with the carboxylated mannan into peritoneal macrophages. In this figure, blue and brown indicate Fe-introduced regions, and red indicates nucleus. This microphotograph is 1000× magnified.

First, uptake efficiency of carboxylated mannan coated SPIONs into antigen presenting cells was investigated. Peritoneal macrophages were selected as model cells of antigen presenting cells. Peritoneal macrophages isolated from Balb/C mice were incubated for 3 hours in the medium supplemented with carboxylated mannan coated SPIONs. Upon completion of the incubation, Prussian blue staining was performed to observe the uptake of carboxylated mannan coated SPIONs into the cells. Prussian blue staining is the method based on the principle that when Fe ions are reacted with ferrocyan compound, ferrocyanide iron compound is generated. Distribution of Fe ions can be confirmed by this staining method. The result is shown in FIG. 6. As shown in FIG. 6, it was confirmed that carboxylated mannan coated SPIONs were successfully introduced into the cells. Therefore, it was suggested that carboxylated mannan coated SPIONs could be used for such target cells as antigen presenting cells or the tissue containing a large amount of those antigen presenting cells. Such intracellular uptake can be explained with endocytosis.

Figure 7:
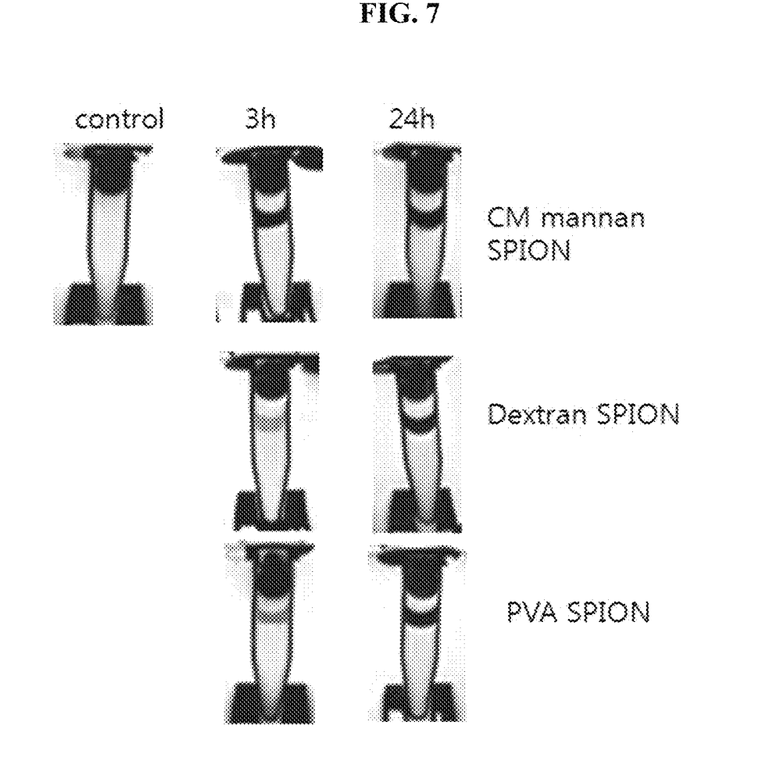
FIG. 7 is MR phantom imaging of peritoneal macrophages incubated with the SPIONs coated with the carboxylated mannan. Cells are located in the center of microcentrifuge tubes.

An additional experiment was performed to compare intracellular uptake efficiency between the MRI contrast agent of the present invention and other MRI contrast agents. Other MRI contrast agents selected for the comparison were dextran-coated SPIONs and PVA-coated SPIONs (Mannan coated SPIONs were excluded at that time). In this experiment, peritoneal macrophages were selected as model cells of antigen presenting cells. Peritoneal macrophages isolated from Balb/C mice were incubated for 3 hours or 24 hours in the medium supplemented with SPIONs coated with carboxylated mannan, dextran or PVA. Upon completion of the incubation, $2\times10^5$ cells were fixed in 5% gelatin, which was transferred in microcentrifuge tube, followed by centrifugation. After the centrifugation, intracellular uptake was investigated by MR phantom imaging. The result is shown in FIG. 7. As shown in FIG. 7, cells turned black as SPIONs were introduced. It was confirmed that carboxylated mannan coated SPIONs were introduced faster than any other SPIONs. This result indicates that carboxylated mannan coated SPIONs are more excellent MRI contrast agent targeting antigen presenting cells or the tissue containing such antigen presenting cells at a high level than any other MRI contrast agents.

<5-3> Measurement of Uptake into Antigen Presenting Cells in Tissues

Figure 8:
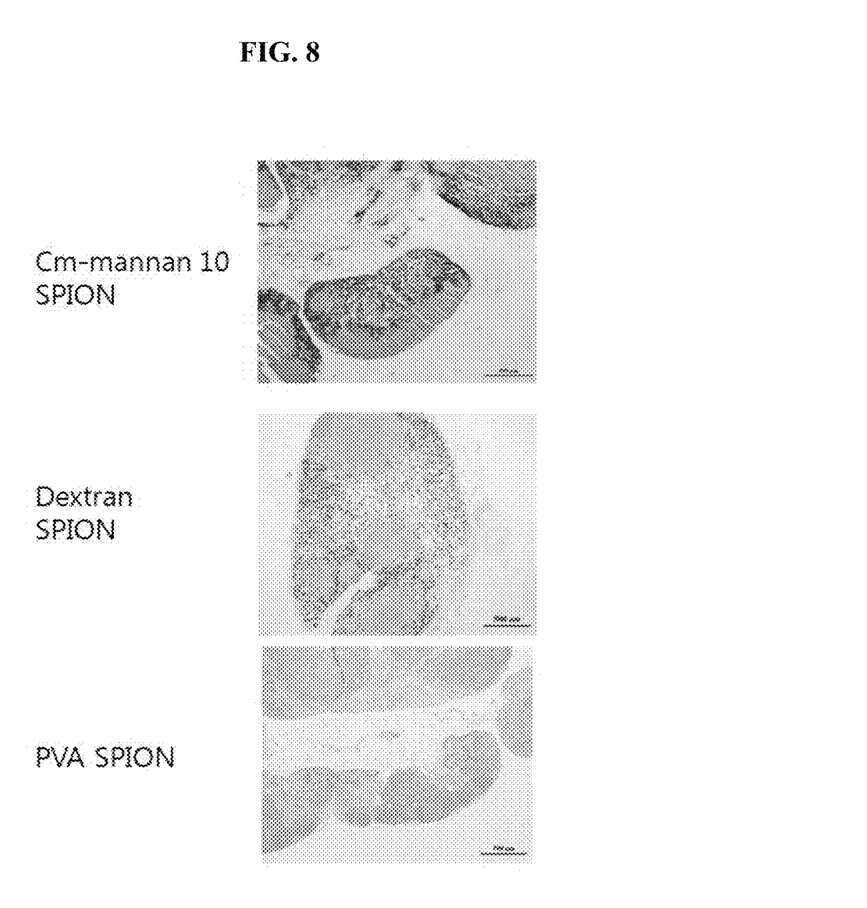
FIG. 8 is a Prussian blue staining result of lymph node treated by three types of MRI contrast agents. In this figure, blue indicates Fe introduced regions.

To investigate the possibility of using carboxylated mannan coated SPIONs as a MRI contrast agent targeting tissues containing antigen presenting cells, intracellular uptake efficiency into antigen presenting cells contained in real tissues was investigated and compared with those of other MRI contrast agents. Macrophages were selected as model cells of antigen presenting cells. As a model tissue, lymph node that contains a large amount of macrophages was selected. After injecting each MRI contrast agent, Prussian blue staining was performed to measure the uptake of each agent. Particularly, after injecting each MRI contrast agent, lymph node tissue was extracted. The extracted lymph node was loaded in 1 ml of formalin solution, which was then fixed in paraffin. Then the fixed lymph node was incised for staining. The lymph node slice was stained with 10% potassium ferrocyanide and 20% HCl for 20 minutes. The stained slice was observed under optical microscope. The result is shown in FIG. 8. The blue dots indicate iron oxide particles. As shown in FIG. 8, carboxylated mannan coated SPIONs were well distributed in lymph node, compared with other MRI contrast agents. Therefore, it was confirmed that carboxylated mannan coated SPIONs can be effectively introduced into antigen presenting cells in tissues, so that it can be effectively used as a MRI contrast agent targeting such tissues that contain antigen presenting cells.

Example 6

Use of Carboxylated Mannan Coated SPIONs for the Diagnosis of Cancer Metastasis to Lymph Node Usability of carboxylated mannan coated SPIONs, particularly in relation to diagnosis of cancer metastasis to lymph node, was compared on MRI with those of the conventional MRI contrast agents, dextran-coated SPIONs and PVA-coated SPIONs. Each contrast agent was administered to each experimental animal showing metastasis to lymph node, at the dose of 1 mg Fe/animal. Then, their lymph nodes were compared one another on MRI. Turbo-spin echo (TSE) T2-weighted (repetition time ms/echo time ms of 3,200/86, flip angle 150°, echo train length of 18, 56 mm field of view, 2 mm section thickness, 0.2-mm intersection gap, 320×320 matrix, 8 NEX) MRI was performed by using a 3 T MR scanner (Siemens Medical System, Elegan, Germany) with 4 channel phased array rat head coil (Rapid Biomedical mdh, Rimpar, Germany) designed by Chonnam National University Hwasun Hospital (Hwasun, Korea). The results are shown in FIGS. 9 and 10.

Figure 9:
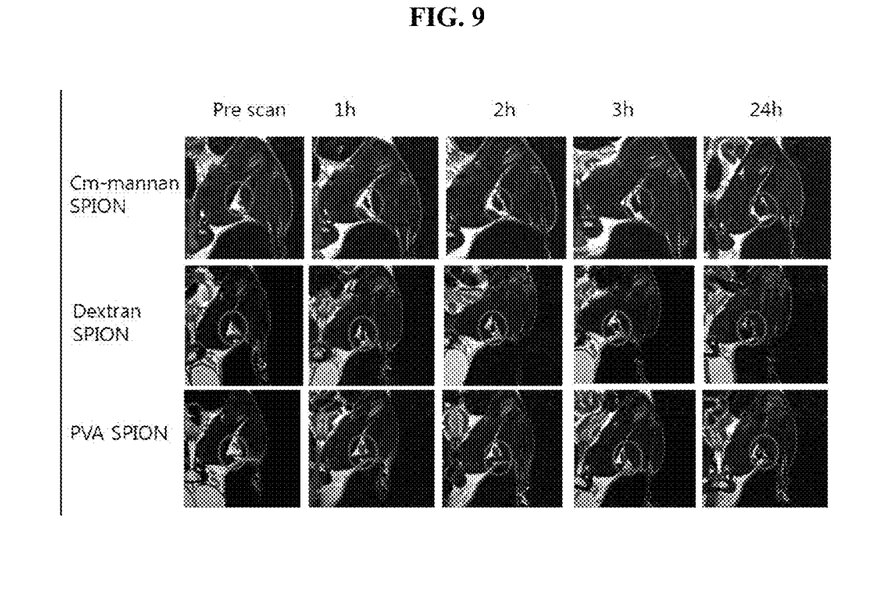
FIG. 9 is a set of photographs illustrating the result of comparing the contrast-enhancement ability in MRI.
Figure 10:
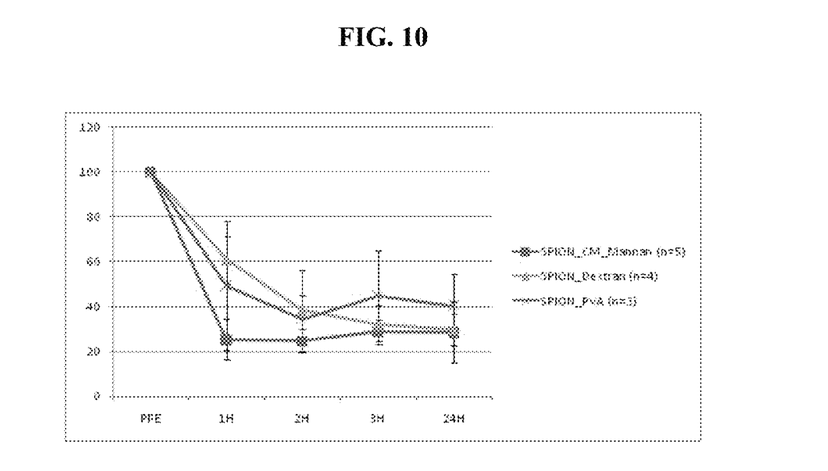
FIG. 10 is a graph illustrating the result of the comparison of the contrast-enhancement ability in MRI with providing signal intensity ratios. The signal intensity ratio indicates the comparative signal strength ratio of lymph node to adjacent muscle.

In FIG. 9, the images obtained from MRI using carboxylated mannan coated SPIONs became more rapidly dark over the time, compared with the images obtained from MRI using controls. This result indicates that carboxylated mannan coated SPIONs can produce big difference in contrast between tissues very fast, so that they can be used as an effective MRI contrast agent for diagnosis of cancer metastasis to lymph node. FIG. 10 shows the comparative ratio of signal intensity of lymph node to that of adjacent muscle. Carboxylated mannan coated SPIONs could be introduced better into lymph node than into muscle, providing stronger signal intensity.

The above results confirmed that the carboxylated mannan coated SPIONs of the present invention could be used as an effective MRI contrast agent targeting tissues containing antigen presenting cells and at the same time could be effectively used as an MRI contrast agent for diagnosis of cancer metastasis to lymph node. That is, the MRI contrast agent of the present invention can be effectively used for the detection of early metastasis of breast cancer, colon cancer and stomach cancer to lymph node.

Example 7

Use for Diagnosis of Sepsis

The present inventors further investigated if the MRI contrast agent of the present invention could be used for the early diagnosis of sepsis. Sepsis is a disease developed by bacterial infection. Once infected by bacteria, the infection area responses against lipopolysaccharide (LPS) of bacteria to produce macrophages at a high level. So, if the produced macrophages could be utilized by any means as an index, sepsis would be more easily detected. The experiment was performed as follows. In the following experiment, the inventors investigated how fast and efficiently carboxylated mannan coated SPIONs could be introduced into the macrophages activated by exposing on LPS.

Figure 11:
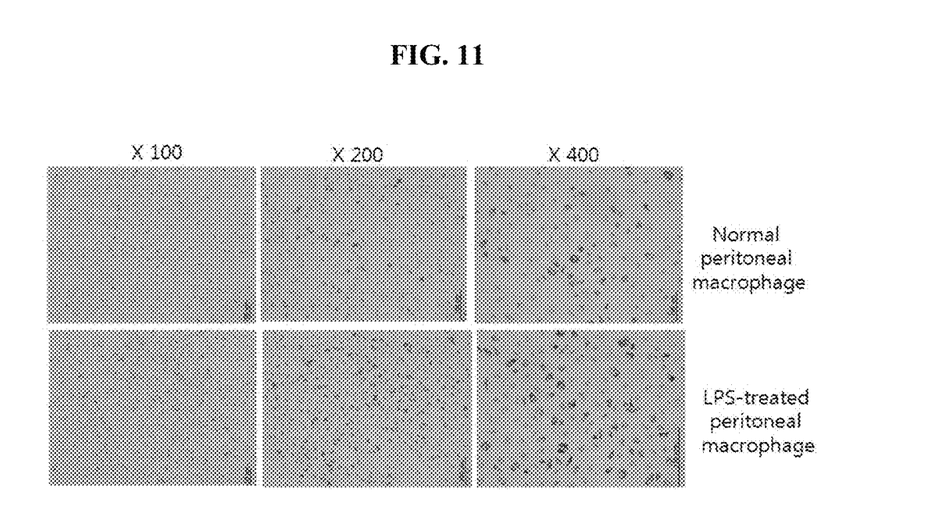
FIG. 11 is a set of photographs illustrating the difference in the intracellular uptake efficiency of SPIONs coated with the carboxylated mannan prepared according to the method of the present invention between LPS-treated cells and normal cells.

A part of peritoneal macrophages was treated with LPS to make it as sepsis like condition. The peritoneal macrophages treated or non-treated with LPS were incubated for 3 hours in the medium supplemented with carboxylated mannan coated SPIONs. Upon completion of the incubation, Prussian blue staining was performed with the cells to investigate the intracellular uptake of carboxylated mannan coated SPIONs. The result is shown in FIG. 11. As shown in FIG. 11, the intracellular uptake of carboxylated mannan coated SPIONs into the cells treated with LPS was significantly increased, compared with in the cells non-treated with LPS. This result indicates that the MRI contrast agent of the present invention could be effectively used for the early diagnosis of sepsis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A superparamagnetic nanoparticle MRI contrast agent coated with carboxylated mannan that has a ring-opened dicarboxylate unit having a formula in between some of the mannose monomers, for visualizing antigen presenting cells and the tissue containing such antigen presenting cells specifically in MRI.

2. The MRI contrast agent according to claim 1, wherein the antigen presenting cells are dendrite cells, macrophages, or B-cells.

3. The MRI contrast agent according to claim 1, wherein the agent is used for the diagnosis of cancer metastasis of lymph node.

4. The MRI contrast agent according to claim 1, wherein the agent is used for the diagnosis of sepsis.

5. The MRI contrast agent according to claim 1, wherein the dicarboxylate unit is produced from an aldehyde-mannan having a ring-opened dialdehyde unit having a formula 6. The MRI contrast agent according to claim 1, wherein at least 10 mol % of the carboxylated mannan comprises the dicarboxylate unit.

7. The MRI contrast agent according to claim 1, wherein the superparamagnetic nanoparticle comprises iron oxide.

8. The MRI contrast agent according to claim 7, wherein the iron oxide is magnetite ($Fe_3O_4$) or maghemite ($Fe_2O_3$).

9. A superparamagnetic nanoparticle MRI contrast agent coated with a carboxylated mannan prepared by a method comprising the following steps:

a) synthesizing superparamagnetic nanoparticles;

b) synthesizing an aldehyde-mannan by introducing a ring-opened dialdehyde unit represented by a formula in between some of the mannose monomers;

c) oxidizing the dialdehyde unit to a dicarboxylate unit represented by a formula to form the carboxylated mannan; and d) coating the synthesized superparamagnetic nanoparticles with the prepared carboxylated mannan.

10. The MRI contrast agent according to claim 9, wherein the contrast agent is used for the diagnosis of cancer metastasis of lymph node.

11. The MRI contrast agent according to claim 9, wherein the contrast agent is used for the diagnosis of sepsis.

12. The MRI contrast agent according to claim 9, wherein at least 10 mol % of the carboxylated mannan comprises the dicarboxylate unit.

13. The MRI contrast agent according to claim 9, wherein the superparamagnetic nanoparticle comprises iron oxide.

14. The MRI contrast agent according to claim 13, wherein the iron oxide is magnetite ($Fe_3O_4$) or maghemite ($Fe_2O_3$).

15. The MRI contrast agent according to claim 9, wherein the dialdehyde unit is produced from opening of a mannose ring through oxidation.

16. The MRI contrast agent according to claim 9, wherein about 13 mol % of the carboxylated mannan comprises the dicarboxylate unit.

17. The MRI contrast agent according to claim 1, wherein the antigen presenting cells are macrophages.

18. The MRI contrast agent according to claim 5, wherein the dialdehyde unit is produced from opening of a mannose ring through oxidation.

* * * * *